United States Patent [19]

Sawai et al.

[11] Patent Number: 4,994,085
[45] Date of Patent: Feb. 19, 1991

[54] ARTIFICIAL STEM UNIT FOR COXA WITH SETTING GUIDE

[75] Inventors: Kazuhiko Sawai, Nagoya; Shigeo Niwa; Tomokazu Hattori, both of Aichi; Wataru Yagi, Nagoya; Ryohei Yabuno; Masami Ishii, both of Toyota, all of Japan

[73] Assignee: Aisin Seiki Kabushiki Kaisha, Kariya, Japan

[21] Appl. No.: 320,436

[22] Filed: Mar. 8, 1989

[30] Foreign Application Priority Data

Mar. 9, 1988 [JP] Japan .................................. 63-55634

[51] Int. Cl.⁵ .............................................. A61F 2/32
[52] U.S. Cl. ......................................... 623/23; 623/16
[58] Field of Search ...................... 623/16, 18, 20, 21, 623/22, 23

[56] References Cited

U.S. PATENT DOCUMENTS

| 3,846,846 | 11/1974 | Fischer | 623/23 |
| 3,906,550 | 9/1975 | Rostoker et al. | 623/23 |
| 4,080,666 | 3/1978 | Fixel | 623/23 |
| 4,337,773 | 7/1982 | Raftopoulos et al. | 623/16 A |
| 4,520,511 | 6/1985 | Gianezio et al. | 623/23 |
| 4,657,549 | 4/1987 | Keller | 623/16 |
| 4,678,471 | 7/1987 | Noble et al. | 623/16 |
| 4,919,673 | 4/1990 | Willert et al. | 623/23 |

FOREIGN PATENT DOCUMENTS

| 0143847 | 6/1985 | European Pat. Off. | 623/16 A |
| 0331623 | 9/1989 | European Pat. Off. | 623/23 |
| 86/02260 | 4/1986 | World Int. Prop. O. | 623/18 |

Primary Examiner—David J. Isabella
Attorney, Agent, or Firm—Banner, Birch, McKie & Beckett

[57] ABSTRACT

An artificial stem unit for coxa with a setting guide comprises a stem made of metal to be inserted into the marrow cavity of a femur and a setting guide for fixing the stem in the marrow cavity comprising a cylindrical core rod and a plug attached to the end of the cylindrical core rod. In the operation, the setting guide is inserted into the marrow cavity of the femur in advance for the centering, and thereafter, the stem is inserted so that the through hole of the stem fit with the cylindrical core rod of the setting guide. Then the bone cement is injected to fix the stem at an accurate position set up by the above operation.

4 Claims, 2 Drawing Sheets

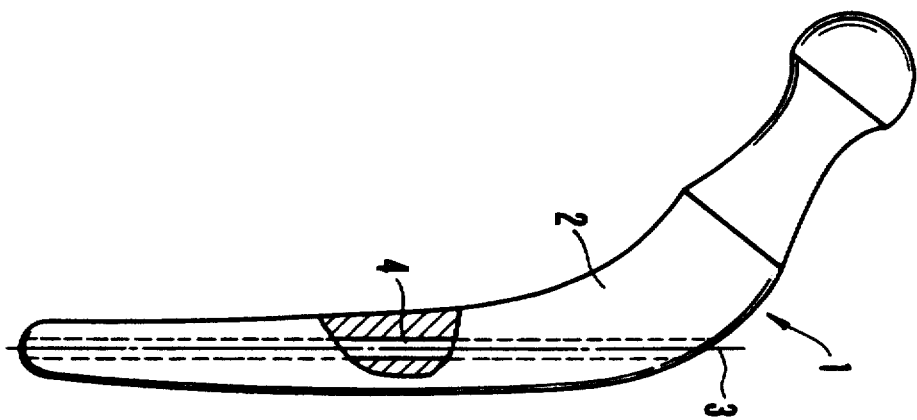
FIG.1(A)
FIG.1(B)
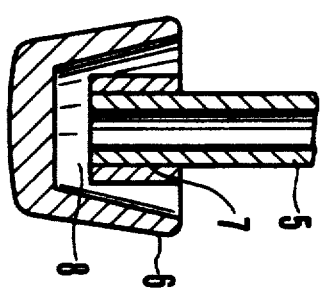
FIG.3
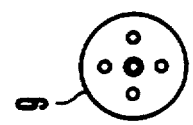
FIG.2(A)
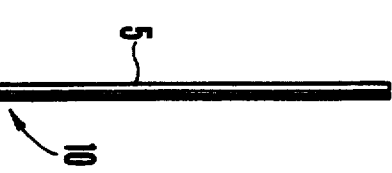
FIG.2(B)

ARTIFICIAL STEM UNIT FOR COXA WITH SETTING GUIDE

BACKGROUND OF THE INVENTION

1. Field of the Invention

This invention relates to an artificial stem unit, which is used as the artificial stem unit for coxa in the case where the coxa of human body suffers from functional disorders in the joint region.

2. Prior Art

An example of conventional artificial heads(stems) of the coxa is illustrated in FIGS. 5 and 6.

In the case mentioned in FIG. 5, bone cement 13 is injected into the cavity of bone marrow to fix a stem 11 inserted by using no centralizer. The numeral 14 represents the cancellous diaphysis and the numeral 15, the femur.

In the case mentioned in FIG. 6, there is inserted beforehand, into the cavity of marrow of a femur forming the diaphysis 14, a centralizer 16 made of bone cement and having a convexity 16a. Then a stem 17 is set within the cavity of the femur marrow and the bone cement 13 is injected into the marrow cavity by means of a cement injector. Thereafter, the stem 17 which is provided at the tip thereof with a concavity 17a conformable to the convexity 16a of said centralizer is pushed into the diaphysis so as to be fit to the centralizer. In this way, the stem may be appropriately positioned within the femur by means of the centralizer.

But the aforementioned conventional device have the following disadvantages.

(1) As the concavity 17a provided at the tip of the stem is shallow, the stem is often fixed in such manner that the central axis A of the joint is slightly out of the central axis B of the stem, unless the stem is skillfully inserted in the diaphysis. Thus, the stem may not sometimes be appropriately positioned within the femur.

(2) When it takes much time to insert the stem 17 into the cavity of the bone marrow 14 for appropriately fitting the stem to said centralizer, the bone cement injected in advance would start to harden and the surgical operation would become uncontrollable. Thus, this type of operation would require a considerable degree of skill.

(3) When the stem 17 is inserted, air would enter in between the stem and the bone cement 13. It may not be possible to remove the air thoroughly. Thus, the strength of adhesion would be lowered.

(4) When the stem is inserted in such manner that it comes off the central axis, the bone cement would not be thoroughly filled up and the pressure may not be evenly placed upon the bone cement.

As described above, there is a problem that the stem may not be accurately positioned, in the stem replacement operation employing the combination of a stem with concavity and a centralizer with small convexity.

SUMMARY OF THE INVENTION

The object of the present invention is to provide an artificial stem unit for coxa with a setting guide, which can be appropriately positioned within the femur, making the operation time to be saved and requiring not so much skill.

In order to achieve this object, the present invention provides a femoral prosthesis system comprising an elongated stem defining a central longitudinal axis configured to be inserted and centered in an intramedullary cavity, said stem having a through bore extending and aligned along the longitudinal axis thereof, said bore having a diameter of about 1.0 to 5.0 mm, and a separate setting guide insertable within the intramedullary cavity before cementing of said stem for aligning the stem in the intramedullary cavity, said setting guide including a cylindrical centering rod and a plug attached to one end of the rod, said rod having an outer diameter sized to slidably fit within the through bore such that the stem is capable of sliding over said rod as the stem is inserted in the intramedullary cavity, whereby proper alignment of said stem is established before the stem is cemented in place. The plug optionally includes a degassing aperture formed therein and optionally includes means for removably coupling the plug to said rod.

In accordance with the present invention, the stem is made of such metal as Ti alloy, Co-Cr-Mo alloy, SUS316L, almina or zirconia. A through hole of 1.0–5.0 mm diameter, is formed in the stem along the central axis thereof. A setting guide is inserted into the diaphysis for fixing and centering the stem. The setting guide comprises a cylindrical core rod made of such materials as bone cement, Ti alloy or stainless alloy, and a plug made of such materials as bone cement, super-high polymer polyethylene or hydroxyapatite. The plug is to hold said core rod and provided with a degassing aperture. The core rod has such length that it protrudes out of the stem when the cylindrical core rod is inserted into the through hole of the stem. The plug may be provided with a plurality of brims at the outer circumference, so that it may be securely positioned.

At the time of operation using the above unit, the inside of the femur diaphysis is excavated. The trial stem is inserted thereinto and the reproduction and confirmation thereof are made. Then, the plug is inserted into the bone marrow, bone cement is injected thereinto and stem is inserted following the guide. In this way, the stem and the plug are inserted in the same manner that said trial stem was inserted. The core rod is either pulled out, immediately before the bone cement gets hardened, or the protruding part of the core rod is removed. Thus, the central axis of the stem coincides with the center of the joint and the air admitted may be discharged through the aperture on the axile center of the stem when the stem is inserted.

The advantages of the present invention are as mentioned below.

(1) The through hole of the stem is caused to be located on the central axis by the setting guide inlaid beforehand along the through hole. Therefore, it becomes possible to perform a replacement operation with an accurate and appropriate positioning of the stem to the extent which has never been heretofore experienced.

(2) The through hole made in the setting guide and the stem of the present invention are highly effective for discharging the air admitted in between the bone cement and the stem.

(3) Further, the stem is inserted into the accurate position and the bone cement is evenly filled up around the stem. The early deterioration and breakdown of the bone cement which has been inevitable due to the cement unevenly set can be avoided. Further, the stem gives the pressure evenly upon the bone cement.

The foregoing and other objects, features and advantages of the present invention will be understood more clearly and fully from the following detailed description of preferred embodiments with reference to the attached drawings.

BRIEF DESCRIPTION OF THE DRAWINGS

FIGS. 1(a) and 1(b) illustrate one embodiment of the stem according to the present invention; FIG. 1(a) showing the view of front elevation thereof, and FIG. 1(b) showing the side elevation thereof.

FIGS. 2(a) and 2(b) illustrate one embodiment of the setting guide according to the present invention; FIG. 2(a) showing the plane view thereof, and FIG. 2(b) showing the side elevation thereof.

FIG. 3 illustrates the enlarged view of one embodiment of the plug according to the present invention.

DESCRIPTION OF THE PREFERRED EMBODIMENTS

Figure 4:
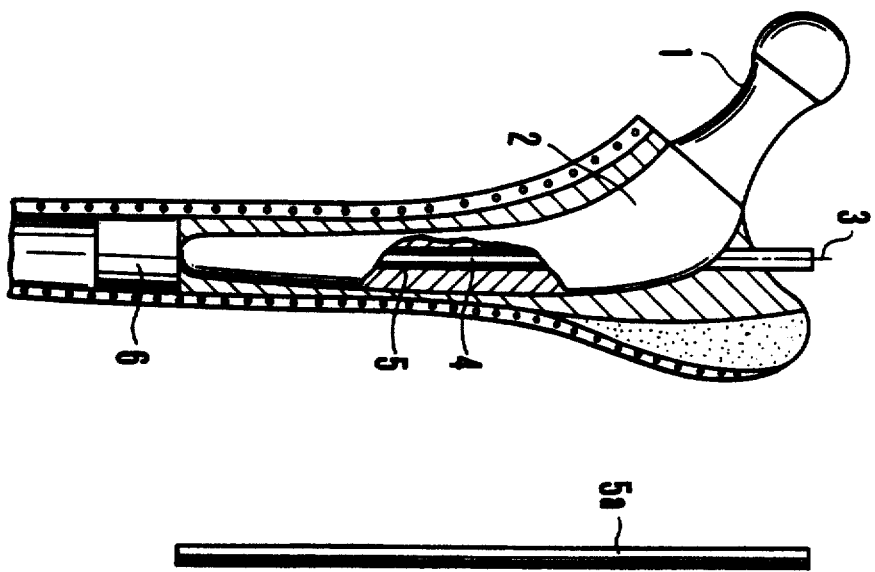
FIG. 4 is an explanatory view in fragmentary section of the stem in the condition inserted in the joint part.
Figure 5:
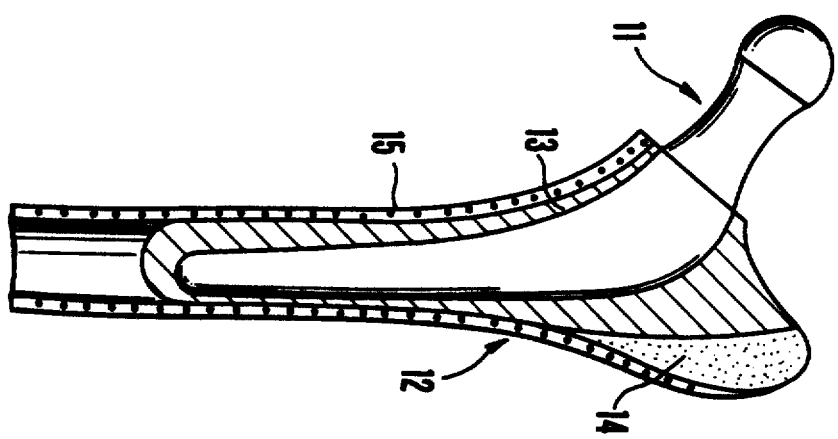
FIG. 5 shows a view of the conventional stem.
Figure 6:
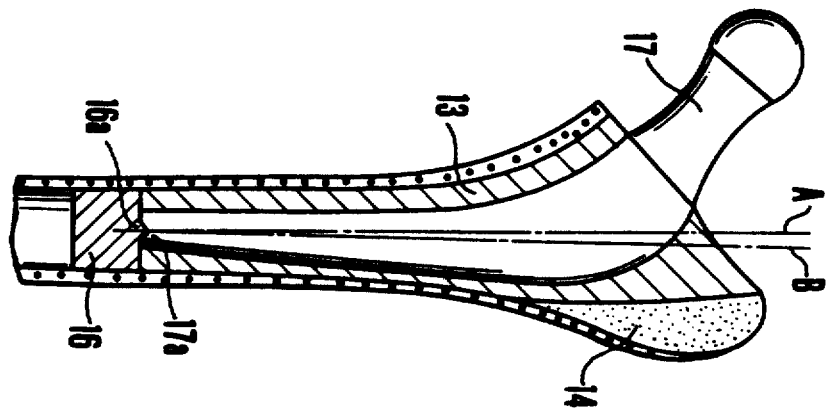
FIG. 6 shows a view in section of another conventional stem.

Referring to the drawings, in FIGS. 1 to 3, the numeral 1 represents the stem made of such materials as Ti alloy, Co-Cr-Mo alloy, SUS316L, almina or zirconia. A through hole 4, slightly larger than 3.0 mm in diameter, is formed along the central axis 3. As illustrated in FIG. 2, a setting guide 10 comprises a core rod 5 and a plug 6. The core rod 5 is slightly smaller than 3.0 mm in diameter. The setting guide is inserted into the through hole 4 of the stem.

As illustrated in FIG. 3, the plug is provided with an insertion part 7 for the core rod 5 and a degassing aperture 8.

The plug and core rod are both made of such materials as bone cement, super-high polymer polyethylene, hydroxyapatite, Ti alloy, Co-Cr-Mo alloy and the like.

The outline of the surgical operation involving the use of said stem 1 and setting guide 10 is as follows:

(1) A pyriformis is cut off for an easier surgical operation at the femur region.

(2) The limb of a patient is put out of joint and held. Then, the neck part, particularly the part near the greater trochanter, is thoroughly excavated by a groove chisel.

(3) The femur diaphysis is curetted by the chisel having the same concave as that of the stem.

(4) The inside of the diaphysis is excavated by the rasp having the shape identical to that of the stem.

(5) The reproduction is made by a trial stem to examine the positioning of the stem and ensure that the stem would not be dislocated.

(6) The plug of the setting guide is adjusted to the shape of the femur diaphysis and aligned to be concentered with the diaphysis.

(7) The bone cement is injected into the diaphysis by the cement injector. At this process, the plug of the setting guide can be useful as the cement leak stopper and for discharging the air admitted.

(8) The stem is pushed into the diaphysis along the setting guide. In this connection, after the stem is inserted, the core rod 5 protruding out of the stem should be pulled out before the bone cement gets hardened or the protruding part be cut off after the cement hardened. In FIG. 4, the numeral 5a represents the core removed.

(9) Thus, it is made possible the desired setting of the joint after the suture of bones and sinews and that of hypodermic parts and skins.

As described above, the central axis A of the joint coincides with the central axis B of the stem in the surgical operation involving the use of the stem unit of the present invention. Further, there is required not much operational skill and the short time operation becomes possible.

It should be understood that, although the preferred embodiment of the present invention has been described herein in considerable detail, certain modifications, changes, and adaptations may be made by those skilled in the art and that it is hereby intended to cover all modifications, changes and adaptations thereof falling within the scope of the appended claims.

What is claimed is:

1. A femoral prosthesis system comprising an elongated stem defining a central longitudinal axis configured to be inserted and cemented in an intramedullary cavity, said stem having a through bore extending and aligned along the longitudinal axis thereof, said bore having a diameter of about 1.0 to 5.0 mm, and a separate setting guide insertable within the intramedullary cavity before cementing of said stem for aligning the stem in the intramedullary cavity, said setting guide having degassing means and including a cylindrical centering rod and a plug attached to one end of the rod, said rod having an outer diameter sized to slidably fit within the through bore such that the stem is capable of sliding over said rod as the stem is inserted in the intramedullary cavity, whereby proper alignment of said stem is established before the stem is cemented in place.

2. The prosthesis system of claim 1 wherein said degassing means comprises a bore within said centering rod, and air passages in said plug communicating between the bore in the centering rod and the cavity surrounding the rod.

3. The prosthesis system of claim 1, wherein said stem is made of metal selected from the group consisting of Ti alloy, Co-Cr-Mo alloy, stainless steel, alumina and zirconia.

4. The prosthesis system of claim 1, wherein said stem is made of material selected from the group consisting of bone cement, Ti alloy and stainless steel.

* * * * *